United States Patent
Shiotani et al.

(10) Patent No.: US 12,002,210 B2
(45) Date of Patent: Jun. 4, 2024

(54) ANALYSIS SOFTWARE AND APPARATUS FOR SCREENING EARLY EMBRYO

(71) Applicant: JCR Pharmaceuticals Co., Ltd., Ashiya (JP)

(72) Inventors: Masahide Shiotani, Kobe (JP); Junko Otsuki, Kobe (JP)

(73) Assignee: JCR Pharmaceuticals Co., Ltd., Ashiya (JP)

(*) Notice: Subject to any disclaimer, the term of this patent is extended or adjusted under 35 U.S.C. 154(b) by 504 days.

(21) Appl. No.: 17/124,729

(22) Filed: Dec. 17, 2020

(65) Prior Publication Data

US 2021/0104046 A1    Apr. 8, 2021

Related U.S. Application Data

(63) Continuation of application No. PCT/JP2019/024593, filed on Jun. 20, 2019.

(30) Foreign Application Priority Data

Jun. 20, 2018    (JP) .................................. 2018-116833

(51) Int. Cl.
*G06K 9/00*    (2022.01)
*A61B 90/00*   (2016.01)
(Continued)

(52) U.S. Cl.
CPC ............ *G06T 7/0016* (2013.01); *A61B 90/20* (2016.02); *A61B 90/361* (2016.02);
(Continued)

(58) Field of Classification Search
CPC ............... C12M 21/06; C12M 41/46; G06T 2207/30044; G06T 7/62; G06T 7/0014;
(Continued)

(56) References Cited

U.S. PATENT DOCUMENTS

2010/0041090 A1*  2/2010  Ramsing ............... C12M 21/06
                                                    435/29
2013/0337487 A1* 12/2013  Loewke ................... G06T 7/68
                                                    435/29
(Continued)

FOREIGN PATENT DOCUMENTS

JP         2015-130806 A      7/2015

OTHER PUBLICATIONS

Peter Kovacs, "Embryo selection: the role of time-lapse monitoring", Reproductive Biology and Endocrinology, 2014, 12:124, pp. 1-11 (Year: 2014).*

(Continued)

*Primary Examiner* — Atiba O Fitzpatrick
(74) *Attorney, Agent, or Firm* — Oblon, McClelland, Maier & Neustadt, L.L.P.

(57) ABSTRACT

Disclosed are a software for analyzing images of a fertilized egg, the software providing a means for executing a process including: (a) a step of measuring the difference in area between the female pronucleus and the male pronucleus from images of a fertilized egg obtained in a period of 1 to 10 hours before the time of occurrence of male and female pronuclear membrane breakdown as a reference; (b) a step of measuring the difference in are between the female pronucleus and the male pronucleus from images of the fertilized egg obtained immediately before the time of occurrence of male and female pronuclear membrane breakdown as the reference; and (c) a step of storing the measured values of the area difference obtained in the step (a) and the area difference obtained in the step (b), to be readable at any time as needed, and an apparatus incorporating this software.

11 Claims, 2 Drawing Sheets

(51) Int. Cl.
    *A61B 90/20*         (2016.01)
    *G06T 7/00*          (2017.01)

(52) U.S. Cl.
    CPC .............. *G06T 2207/10056* (2013.01); *G06T 2207/30024* (2013.01); *G06T 2207/30044* (2013.01)

(58) Field of Classification Search
    CPC ......... G06T 7/0016; G06T 2207/20224; G06T 2207/10056; G06T 2207/10061; G06T 2207/30024; A61B 17/425; A61B 17/43; A61B 17/435; A61B 90/20; C12N 5/0603; C12N 5/0604; C12N 15/873; C12N 2517/10; C12N 5/0609; C12N 5/061; G01N 2800/367; G06V 20/69–698; G06V 2201/04
    See application file for complete search history.

(56) References Cited

U.S. PATENT DOCUMENTS

| | | | | |
|---|---|---|---|---|
| 2014/0087415 | A1* | 3/2014 | Ramsing | G01N 33/5005 435/29 |
| 2014/0206931 | A1* | 7/2014 | Zernicka-Goetz | C12M 41/14 506/10 |
| 2014/0220619 | A1* | 8/2014 | Shen | G01N 33/5091 435/34 |
| 2020/0126233 | A1* | 4/2020 | Shinoda | G06T 7/20 |

OTHER PUBLICATIONS

De los Santos, et al., "Expression of Interleukin-1 System Genes in Human Gametes", Biology of Reproduction, 59, pp. 1419-1424 (1998).

Jurisicova et al., "Variability in the expression of trophectodermal markers β-human chorionic gonadotrophin, human leukocyte antigen-G and pregnancy specific β-1 glycoprotein by the human blastocyst", Human Reproduction, vol. 14, No. 7, pp. 1852-1858 (1999).

Tazuke et al., "Growth Factors and Cytokines in Endometrium, Embryonic Development, and Maternal: Embryonic Interactions", Seminars in Reproductive Endocrinology, vol. 14, No. 3, pp. 231-245 (1996).

Simon et al., "Embryonic Regulation of Integrins {beta}3, {alpha}4, and {alpha}1 in Human Endometrial Epithelial Cells in Vitro", Journal of Clinical Endocrinology and Metabolism, vol. 82, No. 8, pp. 2607-2616 (1997).

Giudice, "Endometrial Growth Factors and Proteins", Seminars in Reproductive Endocrinology, vol. 13, No. 2, pp. 93-101 (1995).

Sheth et al., "Prediction of successful embryo implantation by measuring interleukin-1-alpha and immunosuppressive factor(s) in preimplantation embryo culture fluid", Fertility and Sterility, vol. 55, No. 5, pp. 952-957 (1991).

Baranao et al., "Determination of IL-1 and IL-6 Levels in Human Embryo Culture-Conditioned Media", American Journal of Reproductive Immunology, 37, pp. 191-194 (1997), ISSN 8755-8920.

Licht et al., "On the Role of Human Chorionic Gonadotropin (hCG) in the Embryo-Endometrial Microenvironment: Implications for Differentiation and Implantation", Seminars in Reproductive Medicine, vol. 19, No. 1, pp. 37-47 (2001).

D'Hauterive et al., "Human chorionic gonadotropin and growth factors at the embryonic-endometrial interface control leukemia inhibitory factor (LIF) and interleukin 6 (IL-6) secretion by human endometrial epithelium", Human Reproduction, vol. 19, No. 11, pp. 2633-2643 (2004).

Wakuda et al., "Embryo-dependent induction of embryo receptivity in the mouse endometrium", Journal of Reproduction and Fertility, 115, pp. 315-324 (1999).

Gardner et al., "A prospective randomized trial of blastocyst culture and transfer in in-vitro fertilization", Human Reproduction, vol. 13, No. 12, pp. 3434-4340 (1998).

Scholtes et al., "Blastocyst transfer in day-5 embryo transfer depends primarily on the number of oocytes retrieved and not on age", Fertility and Sterility, vol. 69, No. 1, pp. 78-83 (1998).

Milki et al., "Two-blastocyst transfer has similar pregnancy rates and a decreased multiple gestation rate compared with three-blastocyst transfer", Fertility and Sterility, vol. 72, No. 2, pp. 225-228 (1999).

Gardner et al., "Culture and transfer of human blastocysts increases implantation rates and reduces the need for multiple embryo transfers", Fertility and Sterility, vol. 69, No. 1, pp. 84-88 (1998).

Edwards et al., "Blastocyst stage transfer: pitfalls and benefits", Human Reproduction, vol. 14, No. 1, pp. 1-4 (1999).

Otsuki et al., "Potential of zygotes to produce live births can be identified by the size of the male and female pronuclei just before their membranes break down", Reproductive Medicine and Biology, 16, pp. 200-205 (2017).

International Search Report dated Aug. 27, 2019 in PCT/JP2019/024593, filed Jun. 20, 2019.

Carré, D., et al., "In Vitro Fertilization in Ctenophores: Sperm Entry, Mitosis, and the Establishment of Bilateral Symmetry in *Beroe ovata*", Developmental Biology, vol. 147, pp. 381-391(1991) (1).

Filho, E.S., et al., "A Review on Automatic Analysis of Human Embryo Microscope Images", The Open Biomedical Engineering Journal, vol. 4, pp. 170-177(2010).

\* cited by examiner

ANALYSIS SOFTWARE AND APPARATUS FOR SCREENING EARLY EMBRYO

CROSS-REFERENCE TO RELATED APPLICATIONS

The present application is a continuation of International Application No. PCT/JP2019/024593, filed Jun. 20, 2019, which is based upon and claims the benefits of priority to Japanese Application No. 2018-116833, filed Jun. 30, 2018. The entire contents of all of the above applications are incorporated herein by reference.

FIELD OF THE INVENTION

The present invention relates to an analysis software for screening an early embryo, and an analysis apparatus incorporating a recording medium in which the analysis software is recorded. More particularly, the invention relates to a software that can be used for selecting a fertilized egg to be transplanted into the uterine cavity from fertilized eggs obtained by in vitro fertilization, for example, by conducting observations of the areas of male and female pronuclei prior to male and female pronuclear membrane breakdown (PNMBD) that is observed under a microscope, 4 to 8 hours before the male and female pronuclear membrane breakdown and immediately before the male and female pronuclear membrane breakdown, and to an apparatus including a recording medium in which the software is recorded.

DESCRIPTION OF THE RELATED ART

Human infertility is said to occur in about 10% of all couples. For this reason, there is a great demand for infertility treatment, and infertility treatment is currently being widely carried out. Among the treatments that are carried out as infertility treatment, sperms and ova are directly handled only in artificial insemination and in vitro fertilization. Artificial insemination is a technology involving promoting fertilization by injecting sperms into the vagina near the uterine cervix or directly into the uterus or fallopian tubes using an instrument such as a catheter, and the purpose of the technology is to increase the probability of fertilization by avoiding various obstacles existing until a sperm encounters an ovum. On the other hand, in vitro fertilization is a technology involving collecting ova produced by administering an ovulation inducer to a patient from her body, fertilizing the ova in vitro by mixing them with sperms (insemination), culturing fertilized eggs, and transplanting quarter embryos or eighth embryos generally into the uterine cavity through a catheter, usually on day 2 or 3 of culture. Conventionally, progesterone supplementation for preparing the endometrium is employed to facilitate implantation of the transplanted embryos.

A preimplantation embryo produces several kinds of factors during development in order to emit signals to the mother to inform about the presence of the embryo itself. For example, interleukin-1 (IL-1) is a major factor that regulates the exchange of information between the maternal endometrium and the embryo, and the complete IL-1 system is detected in all stages of development in human embryos (De los Santos M J, et al., Biol Reprod. 59. 1419-24 (1998)). Human chorionic gonadotropin (HCG), which is another embryo-derived factor, has its gene already transcribed in 2-cell stage embryos (Jurisicova A I. et al., Hum Reprod. 14. 1852-8 (1999)). Furthermore, it has been observed that several kinds of embryo-derived factors involved in the exchange of information including these factors are released extracellularly when embryos are cultured in vitro. That is, several kinds of embryo-derived factors that regulate the receptive capacity of the endometrium are detected in the culture supernatant of embryos (Tazuke S I. et al., Semin Reprod Endocrinol. 14. 231-45 (1996); Simon C. et al., J Clin Endocrinol Metab. 82. 2607-16 (1997); Giudice L C. et al., Semin Reprod Endocrinol. 13. 93-101 (1995); Sheth K V. et al., Fertil Steril. 55. 952-7 (1991); Baranao R I. et al., Am J Reprod Immunol. 37. 191-4 (1997); Licht P. et al., Semin Reprod Med. 19. 37-(2001); and Perrier d'Hauterive S. et al., Hum Reprod. 19. 2633-43 (2004)). It is known that an embryo developing in the oviduct induces endometrial differentiation even in vivo (Wakuda K. et al., J Reprod Fertil. 115. 315-24 (1999)). All of these indicate that information exchange occurs between an embryo and the endometrium via the factors produced by the embryo in the early stages of development of the embryo. In fact, it has been revealed that not only a preimplantation embryo in the uterine cavity but also an early embryo in the oviduct can regulate endometrial molecules so that the embryo itself can control implantation (Wakuda K. et al., J Reprod Fertil. 115. 315-24 (1999)).

In recent years, blastocyst implantation, which is a form of in vitro fertilization, has been created as a method of improving the probability of implantation in the human infertility treatment and is clinically practiced (Gardner D K. et al., Hum Reprod. 13. 3434-40 (1998); Scholtes M C. et al., Fertil Steril. 69. 78-83 (1998); and Milki A A. et al., Fertil Steril. 72. 225-8 (1999)). In this transplantation technology, the embryos after in vitro fertilization are cultured to day 5 or 6, and the embryos grown therefrom into blastocysts are injected into the uterine cavity. In blastocyst transfer, physiological synchronization occurs between the endometrium and the developmental stage of the embryo, long-term in vitro culture makes it easy to select an embryo having high implantation ability, and thereby the probability of implantation becomes high compared to that of early embryo transfer (Gardner D K. et al., Fertil Steril. 69. 84-88 (1998); and Edwards R G. et al., Hum Reprod. 14. 1-4 (1999)). While the number of days to reach the implantation is 4 to 5 days for embryos that have been cultured for 2 to 3 days, the number of days to implantation is as short as 1 day in blastocyst transplantation, and the risk of embryo loss to the outside of the uterus is reduced, which is also advantageous for implantation. However, it is still the current situation that the pregnancy rate in human blastocyst transplantation remains at about 36.4%. Implantation failure in blastocyst transplantation is considered to be due to the inability of the blastocyst to hatch from the zona pellucida, or due to the development of the transplanted blastocyst being stopped in the uterine cavity, or the like. As such, since there are many cases in which pregnancy does not occur even with blastocyst transplantation that is currently conducted, there is a demand for a means for further increasing the probability of pregnancy.

In recent years, as a means for increasing the probability of pregnancy, a method of using the areas of the male pronucleus and the female pronucleus of a fertilized egg as parameters has been reported (Otsuki J. et al., Reprod Med Biol. 16. 200-5 (2017)).

PRIOR ART DOCUMENTS

Non-Patent Documents

[Non-patent Document 1] De los Santos M J, et al., Biol Reprod. 59. 1419-24 (1998)

[Non-patent Document 2] Jurisicova A I. et al., Hum Reprod. 14. 1852-(1999)
[Non-patent Document 3] Tazuke S I. et al., Semin Reprod Endocrinol. 14. 231-45 (1996)
[Non-patent Document 4] Simon C. et al., J Clin Endocrinol Metab. 82. 2607-16 (1997)
[Non-patent Document 5] Giudice L C. et al., Semin Reprod Endocrinol. 13. 93-101 (1995)
[Non-patent Document 6] Sheth K V. et al., Fertil Steril. 55. 952-7 (1991)
[Non-patent Document 7] Baranao R I. et al., Am J Reprod Immunol. 37. 191-4 (1997)
[Non-patent Document 8] Licht P. et al., Semin Reprod Med. 19. 37-47 (2001)
[Non-patent Document 9] Perrier d'Hauterive S. et al., Hum Reprod. 19. 2633-43 (2004)
[Non-patent Document 10] Wakuda K. et al., J Reprod Fertil. 115. 315-24 (1999)
[Non-patent Document 11] Gardner D K. et al., Hum Reprod. 13. 3434-40 (1998)
[Non-patent Document 12] Scholtes M C. et al., Fertil Steril. 69. 78-83 (1998)
[Non-patent Document 13] Milki A A. et al., Fertil Steril. 72. 225-8 (1999)
[Non-patent Document 14] Gardner D K. et al., Fertil Steril. 69. 84-88 (1998)
[Non-patent Document 15] Edwards R G. et al., Hum Reprod. 14. 1-4 (1999)
[Non-patent Document 16] Otsuki J. et al., Reprod Med Biol. 16. 200-5 (2017)

SUMMARY OF THE INVENTION

Technical Problem

An object of the invention is to provide a software for providing a means for selecting a fertilized egg to be transplanted into the uterine cavity from fertilized eggs obtained by in vitro fertilization, and an apparatus including a recording medium in which the software is recorded.

Technical Solution

In a study aimed at the above-described objective, the inventors found that the birth rate in in vitro fertilization can be increased by selecting a fertilized egg in which, upon comparing the difference in area between the male and female pronuclei prior to male and female pronuclear membrane breakdown (PNMBD) of fertilized eggs 4 to 8 hours before the male and female pronuclear membrane breakdown and immediately before the male and female pronuclear membrane breakdown, the difference in area between the male and female pronuclei is reduced immediately before the male and female pronuclear membrane breakdown, and transplanting the fertilized egg into the uterine cavity. Thus, the inventors completed the invention. That is, the invention includes the following.

1. A software for analyzing an image of a fertilized egg, the software providing a means for executing a process including the following steps:
   (a) a step of measuring an area difference between the female pronucleus and the male pronucleus from images of a fertilized egg obtained at any time point in the period from 1 hour before to 10 hours before the time of occurrence of male and female pronuclear membrane breakdown as a reference;
   (b) a step of measuring an area difference between the female pronucleus and the male pronucleus from images of a fertilized egg obtained at any time point in the period from immediately before to minutes before the time of occurrence of male and female pronuclear membrane breakdown as a reference; and
   (c) a step of storing the measured values of the area difference obtained in the step (a) and the area difference obtained in the step (b), with the measured values being readable at any time as needed.

2. The software according to 1 above, wherein the software is to provide a means for executing a process further including: (d) a step of selecting a measured value capable of satisfying preset criteria, from the measured values obtained in the step (a) and the step (b).

3. The software according to 1 or 2 above, wherein the preset criteria include the following criteria:
   (a') the difference in area between the female pronucleus and the male pronucleus measured at any time point in the period from immediately before to 20 minutes before the time of occurrence of male and female pronuclear membrane breakdown as a reference, is less than 40 $\mu m^2$; and
   (b') the difference in area between the female pronucleus and the male pronucleus measured at any time point in the period from immediately before to 20 minutes before the time of occurrence of male and female pronuclear membrane breakdown as a reference, is reduced as compared to the difference in area between the female pronucleus and the male pronucleus measured at any time point in the period from 7 hours before to 10 hours before the time of occurrence.

4. The software according to 1 or 2 above, wherein the preset criteria include the following criteria:
   (c') the difference in area between the female pronucleus and the male pronucleus measured at any time point in the period from immediately before to 20 minutes before the time of occurrence of male and female pronuclear membrane breakdown as a reference, is less than 40 $\mu m^2$; and
   (d') when the difference in area between the female pronucleus and the male pronucleus measured at any time point in the period from immediately before to 20 minutes before the time of occurrence of male and female pronuclear membrane breakdown as a reference, is designated as 1, the difference in area measured at any time point in the period from 7.5 hours before to 8.5 hours before the time of occurrence is 1.3 or greater.

5. The software according to 3 or 4 above, wherein the preset criteria further include:
   (e') the area ratio of the female pronucleus and the male pronucleus (male pronucleus/female pronucleus) measured at any time point in the period from immediately after to 8 hours after the time of occurrence of pronuclear formation as a reference, is always greater than 1.

6. A recording medium having the software according to any one of 1 to 5 above recorded therein.

7. An apparatus comprising: a microscope; a digital camera for capturing images of a fertilized egg observed under the microscope; a memory for storing the images of the fertilized egg captured with the digital camera; the recording medium according to 6 above having a software recorded therein, the software being intended for analyzing the images stored in the memory; and a display unit for displaying the results obtained by the analysis.

8. The apparatus according to 7 above, wherein the apparatus further comprises a cell incubator, and the microscope is disposed so as to capture images of a fertilized egg in a state of being cultured in the cell incubator, at a predetermined interval of time.

9. The apparatus according to 7 or 8 above, wherein the capturing of image is performed at an interval of 1 minute to 5 minutes.

Effect of Invention

According to the invention, for example, the success rate of in vitro fertilization can be increased.

BRIEF DESCRIPTION OF THE DRAWINGS

FIG. 1A shows the changes in the areas of a group that finally gave birth after transplantation, and FIG. 1B shows the changes in the areas of a group that did not give birth after transplantation. The axis of ordinate represents the area ($\mu m^2$), and the axis of abscissa represents the time (h) measured with respect to the time of occurrence of male and female pronuclear membrane breakdown as the reference. A solid rhombus represents the area of the female pronucleus, and a solid circle represents the area of the female pronucleus.

FIG. 2A shows the changes in the areas of a group that finally gave birth after transplantation, and FIG. 2B shows the changes in the areas of a group that did not give birth after transplantation. The axis of ordinate represents the area ($\mu m^2$), and the axis of abscissa represents the time (h) measured with respect to the time of occurrence of male and female pronuclear membrane breakdown as the reference. A solid rhombus represents the area of the female pronucleus, and a solid circle represents the area of the female pronucleus.

DESCRIPTION OF EMBODIMENTS

Figure 1A:
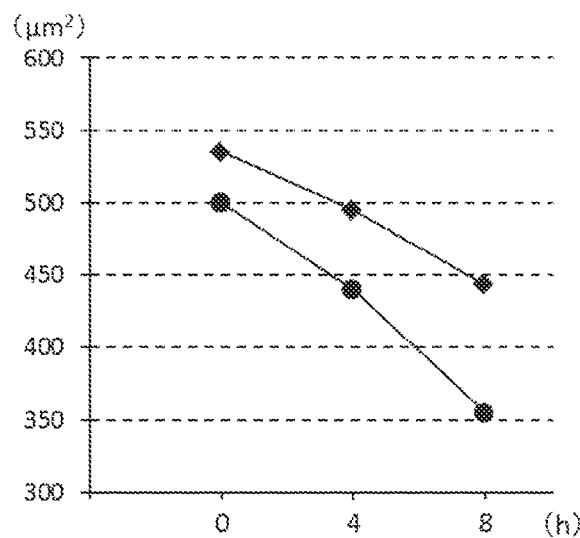
FIGS. 1A and 1B are diagrams showing changes in the areas of the female pronucleus and the male pronucleus in a fertilized egg that has been fertilized by an insemination method (IVF), as measured immediately before (before 0 hour), 4 hours before, and 8 hours before the time of occurrence of male and female pronuclear membrane breakdown as a reference.
Figure 1B:
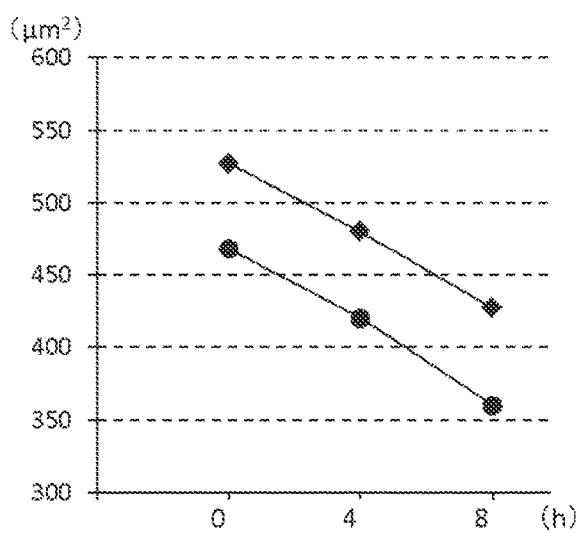
Figure 2A:
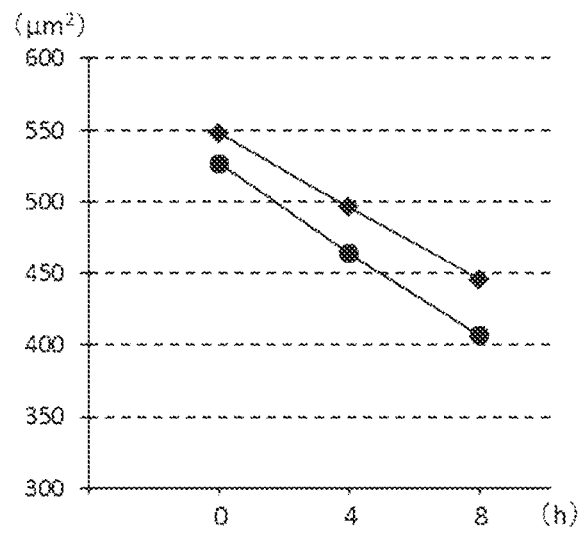
FIGS. 2A and 2B are diagrams showing changes in the areas of the female pronucleus and the male pronucleus in a fertilized egg that has been fertilized by an intracytoplasmic sperm injection method (ICSI), as measured immediately before (before 0 hour), 4 hours before, and 8 hours before the time of occurrence of male and female pronuclear membrane breakdown as a reference.
Figure 2B:
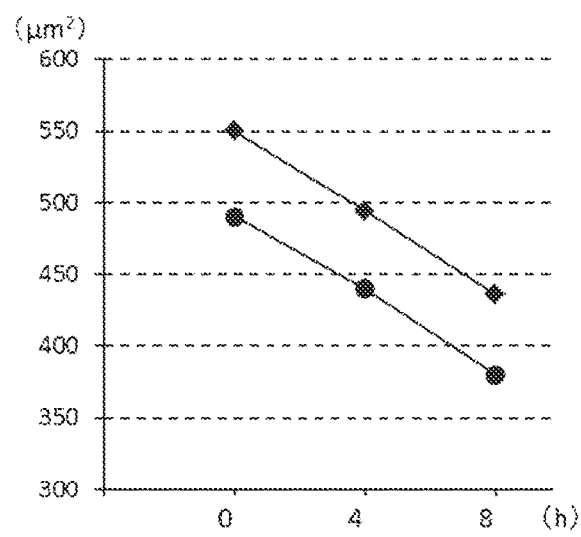

The term "fertilization" as used in the invention refers to a time point at which a sperm has entered the cytoplasm of an egg cell. Furthermore, when the term fertilized egg is used in the invention, the term means an ovum that has been fertilized. Release of the second polar body occurs about 2 hours after fertilization, and about 2 hours after the release of the second polar body, female pronucleus and male pronucleus are observed. The time point at which the female pronucleus and the male pronucleus are observed is referred to as pronuclear formation. Both the female pronucleus and the male pronucleus break down 15 to 21 hours after pronuclear formation. This phenomenon in which the female pronucleus and the male pronucleus break down is referred to as male and female pronuclear membrane breakdown (acronym: PNMBD). The time taken from fertilization to the male and female pronuclear membrane breakdown is approximately 19 to 25 hours.

Measurement of the areas of the female pronucleus and the male pronucleus is carried out based on images obtained by observing a fertilized egg under a microscope. There are no limitations on the technique for calculating such an area (including a calculation formula), and for example, such an area can be determined by the following formula: area of female pronucleus=$\pi \times \frac{1}{2} \times$diameter in horizontal direction$\times \frac{1}{2} \times$diameter in vertical direction ($\mu m^2$), by designating the maximum width in the horizontal direction of the female pronucleus as the diameter in the horizontal direction, and designating the maximum width in the vertical direction as the diameter in the vertical direction. The same also applies to the area of the male pronucleus.

According to the invention, the areas of the female pronucleus and the male pronucleus are measured over time. The interval of measurement is preferably every 5 minutes to every 1 hour, more preferably every 10 minutes to every 30 minutes, and even more preferably every 8 minutes to every 20 minutes, and the measurement interval is, for example, every 5 minutes, every 10 minutes, every 15 minutes, or every 20 minutes.

It is preferable that the measurement of the areas of the female pronucleus and the male pronucleus is initiated before pronuclear formation occurs and is carried out until the male and female pronuclear membrane breakdown. However, the measurement of the area may be initiated immediately after fertilization, and even after male and female pronuclear membrane breakdown, measurement may be continued until the fertilized egg is used for transplantation.

Here, in the measurement of the areas of the female pronucleus and the male pronucleus, the phrase "immediately after the time of occurrence of pronuclear formation as the reference" means the time point of observation at which, regarding images of a fertilized egg observed over time, an image in which pronuclear formation is recognized was obtained for the first time. Furthermore, when it is said to be 6 hours after the time of occurrence of pronuclear formation as the reference, the phrase means the time point of observation at which an image in which pronuclear formation is recognized was obtained for the first time, or the time point of observation immediately before the time point of observation at which an image in which pronuclear formation is recognized was obtained for the first time.

The measurement of the areas of the female pronucleus and the male pronucleus with respect to the time of occurrence of pronuclear formation as the reference will be described in detail below. This measurement of the areas is preferably carried out at any time point in the period from immediately after to 12 hours after the time of occurrence of pronuclear formation; more preferably at any time point in the period from immediately after to 10 hours after the time of occurrence of pronuclear formation; and even more preferably at any time point in the period from immediately after to 8 hours after the time of occurrence of pronuclear formation. The measurement of the areas is not limited to this and may also be carried out at any time point in the period from immediately after to 6 hours after the time of occurrence of pronuclear formation, or at any time point in the period from immediately after to 4 hours after the time of occurrence of pronuclear formation. The measurement may be carried out once or may be carried out two or more times. Usually, the measurement is carried out over time, and the measurement interval is preferably every 5 minutes to every 1 hour, more preferably every 10 minutes to every 30 minutes, and even more preferably every 10 minutes to every 20 minutes. For example, the measurement is carried out at every 5 minutes, every 10 minutes, every 15 minutes, or every 20 minutes. During this period, it is preferable that the area ratio of the female pronucleus and the male pronucleus (male pronucleus/female pronucleus) is always greater than 1.

Next, the measurement of the areas of the female pronucleus and the male pronucleus with respect to the time of occurrence of male and female pronuclear membrane breakdown as the reference will be described in detail below. The measurement of the area is necessarily carried out at any time point in the period from immediately before to 20 minutes before the time of occurrence of the male and female pronuclear membrane breakdown as the reference, or at any time point in the period from immediately before to 30 minutes before the time of occurrence as the reference. Here, the phrase "immediately before the time of occurrence of male and female pronuclear membrane breakdown as the reference" means the time point of observation immediately before a point at which, regarding images of a fertilized egg observed over time, an image in which breakdown of both male and female pronuclear membranes is recognized was obtained. Furthermore, when it is said to be 30 minutes before to 16 hours before the time of occurrence of male and female pronuclear membrane breakdown as the reference, the phrase means the time point of observation immediately before the time point of observation at which an image in which breakdown of both male and female pronuclear membranes is recognized was obtained, or 30 minutes before to 16 hours before the time point of observation at which an image in which breakdown of both male and female pronuclear membranes is recognized was obtained.

Furthermore, the measurement of the areas is preferably carried out one to three times between 1 hour to 16 hours with respect to the time of occurrence of male and female pronuclear membrane breakdown as the reference. In a case in which the measurement is carried out once during this period, the timing is, for example, preferably 4 hours before to 12 hours before, more preferably 6 hours before to 12 hours before, and even more preferably 8 hours before to 12 hours before the time of occurrence of male and female pronuclear membrane breakdown as the reference, and the timing is, for example, 4 hours before, 6 hours, before, 8 hours, before, or 10 hours before the time of occurrence as the reference. In a case in which the measurement is carried out two times during this period, the timing is, for example, preferably 6 hours before to 12 hours before and 3 hours before to 5 hours before, more preferably 7 hours before to 10 hours before and 3.5 hours before to 4.5 hours before, and even more preferably 7.5 hours before to 8.5 hours before and 3.5 hours before to 4.5 hours before the time of occurrence of male and female pronuclear membrane breakdown as the reference. The timing is, for example, 4 hours before and 8 hours before, or 4 hours before and 10 hours before.

The area difference between the female pronucleus and the male pronucleus is determined from the areas of the female pronucleus and the male pronucleus measured over time. Since the area of the male pronucleus is larger than that of the female pronucleus, the area difference between the female pronucleus and the male pronucleus can be determined by the formula: (area difference)=(area of male pronucleus)−(area of female pronucleus).

As an effect according to an embodiment of the invention, increasing the success rate of in vitro fertilization may be mentioned. For that purpose, the areas of the female pronucleus and the male pronucleus measured over time can be used as parameters. In the following description, the use of those areas as parameters in an insemination method (IVF) and an intracytoplasmic sperm injection method (ICSI), respectively and separately, will be described in detail.

The use of the areas as parameters in IVF will be described below by way of examples. In IVF, the areas of the female pronucleus and the male pronucleus are respectively measured 7.5 hours before to 8.5 hours before (particularly, 8 hours before), 3.5 hours before to 4.5 hours before (particularly, 4 hours before), and immediately before the time of occurrence of male and female pronuclear membrane breakdown as a reference. In this way, a fertilized egg that conforms to the selection criteria 1 to 6 shown in Table 1 is selected as the fertilized egg to be used for transplantation. The selection criteria 1 to 6 can be used singly or in combination, and for example, selection criterion 1 may be combined with any of selection criteria 2 to 4, or any of selection criteria 1 to 4 may be combined with selection criterion 5. Furthermore, it is also possible to combine selection criterion 5 with a combination of selection criterion 1 and any of selection criteria 2 to 4, and further combine the resulting combination with selection criterion 6.

TABLE 1

Selection criteria to be applied to fertilized eggs that have been fertilized by IVF (example 1)

| | |
|---|---|
| Selection criterion 1 | The differences in area between the female pronucleus and the male pronucleus measured immediately before to 20 minutes before, 3.5 hours before to 4.5 hours before, and 7.5 hours before to 8.5 hours before the time of occurrence of male and female pronuclear membrane breakdown as a reference are reduced over time. |
| Selection criterion 2 | The difference in area between the female pronucleus and the male pronucleus measured immediately before to 20 minutes before the time of occurrence of male and female pronuclear membrane breakdown as the reference is reduced as compared to the same difference measured 7.5 hours before to 8.5 hours before the time of occurrence as the reference. |
| Selection criterion 3 | When the difference in area between the female pronucleus and the male pronucleus measured immediately before to 20 minutes before the time of occurrence of male and female pronuclear membrane breakdown as the reference is designated as 1, the same differences measured 7.5 hours before to 8.5 hours before and 3.5 hours before to 4.5 hours before the time of occurrence as the reference are 1.6 or greater and 1.4 or greater, respectively. |
| Selection criterion 4 | When the difference in area between the female pronucleus and the male pronucleus measured immediately before to 20 minutes before the time of occurrence of male and female pronuclear membrane breakdown as the reference is designated as 1, the same difference measured 7.5 hours before to 8.5 hours before the time of occurrence as the reference is 1.6 or greater. |
| Selection criterion 5 | When the difference in area between the female pronucleus and the male pronucleus measured immediately before to 20 minutes before the time of occurrence of male and female pronuclear membrane breakdown as the reference is designated as 1, the same difference measured 3.5 hours before to 4.5 hours before the time of occurrence as the reference is 1.4 or greater. |
| Selection criterion 6 | The difference in area between the female pronucleus and the male pronucleus measured immediately before to 20 minutes before the time of occurrence of male and female pronuclear membrane breakdown as the reference is less than 40 μm². |
| Selection criterion 7 | The area ratio of the female pronucleus and the male pronucleus (male pronucleus/female pronucleus) measured at any time point in the period from immediately after to 8 hours after the time of occurrence of pronuclear formation as a reference is always greater than 1. |

The selection criteria 1 to 7 in Table 1 are only for illustrative purposes. With regard to the selection criteria 1 to 6, the condition "immediately before to 20 minutes before" may be, for example, "immediately before", "immediately before to 10 minutes before", or "immediately before to 30 minutes before". Furthermore, with regard to the selection criteria 1 to 4, the condition "7.5 hours before to 8.5 hours before" may also be, for example, "8 hours before", "7 hours before to 9 hours before", or "7 hours before to 10 hours before". Also, with regard to the selection criteria 1 to 3 and 5, the condition "3.5 hours before to 4.5 hours before" may be, for example, "4 hours before", "3.0 hours before to 5.0 hours before", or "4 hours before to 5 hours before".

With regard to the selection criterion 3, it is one of preferred embodiments that when the difference in area between the female pronucleus and the male pronucleus measured immediately before the male and female pronuclear membrane breakdown as the reference is designated as 1, the same differences measured 7.5 hours before to 8.5 hours before (particularly, 8 hours before) and 3.5 hours before to 4.5 hours before (particularly, 4 hours before) are 1.6 or greater and 1.4 or greater, respectively; however, the criterion is not limited to this. For example, the same difference measured 7.5 hours before to 8.5 hours before (particularly, 8 hours before) is preferably 1.5 or greater, more preferably 1.6 or greater, and even more preferably 1.8 or greater. Furthermore, the same difference measured 3.5 hours before to 4.5 hours before (particularly, 4 hours before) is preferably 1.3 or greater, more preferably 1.4 or greater, and even more preferably 1.6 or greater. The same applies also to the selection criteria 4 and 5.

With regard to the selection criterion 6, it is one of preferred embodiments of the invention that the difference in area between the female pronucleus and the male pronucleus measured immediately before the time of occurrence of male and female pronuclear membrane breakdown as the reference is less than 40 $\mu m^2$; however, the criterion is not limited to this. For example, the same difference is less than 45 $\mu m^2$, more preferably less than 40 $\mu m^2$, and even more preferably 35 $\mu m^2$.

With regard to the selection criterion 7, the condition "immediately after to 8 hours after" may also be, for example, "immediately after to 4 hours after", "immediately after to 6 hours after", "immediately after to 10 hours after", or "immediately after to 12 hours after".

The use of the above-described areas as parameters in ICSI will be described below by way of examples. In ICSI, the areas of the female pronucleus and the male pronucleus are respectively measured 7.5 hours before to 8.5 hours before (particularly, 8 hours before), 3.5 hours before to 4.5 hours before (particularly, 4 hours before), and immediately before the time of occurrence of male and female pronuclear membrane breakdown as the reference. In this way, a fertilized egg that conforms to the selection criteria 1 to 7 shown in Table 2 is selected as the fertilized egg to be used for transplantation. The selection criteria 1 to 7 can be used singly or in combination, and for example, any of the selection criteria 1 to 5 may be combined, or any of selection criteria 1 to 5 may be combined with selection criterion 6. Furthermore, it is also possible to combine any of selection criteria 1 to 5 with selection criterion 6, and further combine the resulting combination with selection criterion 7.

TABLE 2

Selection criteria to be applied to fertilized eggs that have been fertilized by ICSI

| | |
|---|---|
| Selection criterion 1 | The differences in area between the female pronucleus and the male pronucleus measured immediately before to 20 minutes before, 3.5 hours before to 4.5 hours before, and 7.5 hours before and 8.5 hours before the time of occurrence of male and female pronuclear membrane breakdown as a reference are reduced over time. |
| Selection criterion 2 | The difference in area between the female pronucleus and the male pronucleus measured immediately before to 20 minutes before the time of occurrence of male and female pronuclear membrane breakdown as the reference is reduced as compared to the same difference measured 7.5 hours before to 8.5 hours before the time of occurrence as the reference. |
| Selection criterion 3 | When the difference in area between the female pronucleus and the male pronucleus measured immediately before to 20 minutes before the time of occurrence of male and female pronuclear membrane breakdown as the reference is designated as 1, the same differences measured 7.5 hours before to 8.5 hours before and 3.5 hours before to 4.5 hours before the time of occurrence as the reference are 1.4 or greater and 1.2 or greater, respectively. |
| Selection criterion 4 | When the difference in area between the female pronucleus and the male pronucleus measured immediately before to 20 minutes before the time of occurrence of male and female pronuclear membrane breakdown as the reference is designated as 1, the same difference measured 7.5 hours before to 8.5 hours before the time of occurrence as the reference is 1.4 or greater. |
| Selection criterion 5 | When the difference in area between the female pronucleus and the male pronucleus measured immediately before to 20 minutes before the time of occurrence of male and female pronuclear membrane breakdown as the reference is designated as 1, the same difference measured 3.5 hours before to 4.5 hours before the time of occurrence as the reference is 1.2 or greater. |
| Selection criterion 6 | The difference in area between the female pronucleus and the male pronucleus measured immediately before to 20 minutes before the time of occurrence of male and female pronuclear membrane breakdown as the reference is less than 30 $\mu m^2$. |
| Selection criterion 7 | The area ratio of the female pronucleus and the male pronucleus (male pronucleus/female pronucleus) measured at any time point in the period from immediately after to 8 hours after the time of occurrence of pronuclear formation as a reference is always greater than 1. |

The selection criteria 1 to 7 in Table 2 are only for illustrative purposes. With regard to the selection criteria 1 to 6, the condition "immediately before to 20 minutes before" may be, for example, "immediately before", "immediately before to 10 minutes before", or "immediately before to 30 minutes before". Furthermore, with regard to the selection criteria 1 to 4, the condition "7.5 hours before to 8.5 hours before" may also be, for example, "8 hours before", "7 hours before to 9 hours before", or "7 hours before to 10 hours before". Also, with regard to the selection criteria 1 to 3 and 5, the condition "3.5 hours before to 4.5 hours before" may be, for example, "4 hours before", "3.0 hours before to 5.0 hours before", or "4 hours before to 5 hours before".

With regard to the selection criterion 3, it is one of preferred embodiments that when the difference in area between the female pronucleus and the male pronucleus measured immediately before the male and female pronuclear membrane breakdown as the reference is designated as 1, the same differences measured 7.5 hours before to 8.5 hours before (particularly, 8 hours before) and 3.5 hours before to 4.5 hours before (particularly, 4 hours before) are 1.4 or greater and 1.2 or greater, respectively; however, the criterion is not limited to this. For example, the same difference measured 7.5 hours before to 8.5 hours before (particularly, 8 hours before) is preferably 1.3 or greater, more preferably 1.4 or greater, and even more preferably 1.5 or greater. Furthermore, the same difference measured 3.5 hours before to 4.5 hours before (particularly, 4 hours before) is preferably 1.1 or greater, more preferably 1.2 or greater, and even more preferably 1.3 or greater. The same applies also to the selection criteria 4 and 5.

With regard to the selection criterion 6, it is one of preferred embodiments of the invention that the difference in area between the female pronucleus and the male pronucleus measured immediately before the time of occurrence of male and female pronuclear membrane breakdown as the reference is less than 30 μm$^2$; however, the criterion is not limited to this. For example, the same difference is less than 35 μm$^2$, more preferably less than 30 μm$^2$, and even more preferably 25 μm$^2$.

With regard to the selection criterion 7, the condition "immediately after to 8 hours after" may also be, for example, "immediately after to 4 hours after", "immediately after to 6 hours after", "immediately after to 10 hours after", or "immediately after to 12 hours after".

The use of the above-described areas as parameters in IVF and ICSI have been described by way of examples as shown above, and the selection criteria to be applied in a case in which fertilized eggs that have been fertilized by IVF and ICSI are not discriminated will be described in Table 3. A situation in which it is not clear which of the selection criteria of IVF and ICSI should be applied is difficult to imagine; however, these selection criteria are selection criteria to be applied under such circumstances. In this case, the areas of the female pronucleus and the male pronucleus are respectively measured 7.5 hours before to 8.5 hours before (particularly, 8 hours before), 3.5 hours before to 4.5 hours before (particularly, 4 hours before), and immediately before the time of occurrence of male and female pronuclear membrane breakdown as the reference. In this way, a fertilized egg that conforms to the selection criteria 1 to 7 shown in Table 2 is selected as the fertilized egg to be used for transplantation. The selection criteria 1 to 7 can be used singly or in combination, and for example, any of the selection criteria 1 to 5 may be combined, or any of selection criteria 1 to 5 may be combined with selection criterion 6. Furthermore, it is also possible to combine any of selection criteria 1 to 5 with selection criterion 6, and further combine the resulting combination with selection criterion 7.

TABLE 3

Selection criteria to be applied in case where fertilized eggs that have been fertilized by IVF and ICSI are not discriminated

| | |
|---|---|
| Selection criterion 1 | The differences in area between the female pronucleus and the male pronucleus measured immediately before to 20 minutes before, 3.5 hours before to 4.5 hours before, and 7.5 hours before and 8.5 hours before the time of occurrence of male and female pronuclear membrane breakdown as a reference are reduced over time. |
| Selection criterion 2 | The difference in area between the female pronucleus and the male pronucleus measured immediately before to 20 minutes before the time of occurrence of male and female pronuclear membrane breakdown as the reference is reduced as compared to the same difference measured 7.5 hours before to 8.5 hours before the time of occurrence as the reference. |
| Selection criterion 3 | When the difference in area between the female pronucleus and the male pronucleus measured immediately before to 20 minutes before the time of occurrence of male and female pronuclear membrane breakdown as the reference is designated as 1, the same differences measured 7.5 hours before to 8.5 hours before and 3.5 hours before to 4.5 hours before the time of occurrence as the reference are 1.4 or greater and 1.2 or greater, respectively. |
| Selection criterion 4 | When the difference in area between the female pronucleus and the male pronucleus measured immediately before to 20 minutes before the time of occurrence of male and female pronuclear membrane breakdown as the reference is designated as 1, the same difference measured 7.5 hours before to 8.5 hours before the time of occurrence as the reference is 1.4 or greater. |
| Selection criterion 5 | When the difference in area between the female pronucleus and the male pronucleus measured immediately before to 20 minutes before the time of occurrence of male and female pronuclear membrane breakdown as the reference is designated as 1, the same difference measured 3.5 hours before to 4.5 hours before the time of occurrence as the reference is 1.2 or greater. |
| Selection criterion 6 | The difference in area between the female pronucleus and the male pronucleus measured immediately before to 20 minutes before the time of occurrence of male and female pronuclear membrane breakdown as the reference is less than 40 μm$^2$. |
| Selection criterion 7 | The area ratio of the female pronucleus and the male pronucleus (male pronucleus/female pronucleus) measured at any time point in the period from immediately after to 8 hours after the time of occurrence of pronuclear formation as a reference is always greater than 1. |

The selection criteria 1 to 7 in Table 3 are only for illustrative purposes. With regard to the selection criteria 1 to 6, the condition "immediately before to 20 minutes before" may be, for example, "immediately before", "immediately before to 10 minutes before", or "immediately before to 30 minutes before". Furthermore, with regard to the selection criteria 1 to 4, the condition "7.5 hours before to 8.5 hours before" may also be, for example, "8 hours before", "7 hours before to 9 hours before", or "7 hours before to 10 hours before". Also, with regard to the selection criteria 1 to 3 and 5, the condition "3.5 hours before to 4.5 hours before" may be, for example, "4 hours before", "3.0 hours before to 5.0 hours before", or "4 hours before to 5 hours before".

With regard to the selection criterion 3, it is one of preferred embodiments that when the difference in area between the female pronucleus and the male pronucleus measured immediately before the male and female pronuclear membrane breakdown as the reference is designated as 1, the same differences measured 7.5 hours before to 8.5 hours before (particularly, 8 hours before) and 3.5 hours before to 4.5 hours before (particularly, 4 hours before) are 1.4 or greater and 1.2 or greater, respectively; however, the criterion is not limited to this. For example, the same difference measured 7.5 hours before to 8.5 hours before (particularly, 8 hours before) is preferably 1.3 or greater, more preferably 1.4 or greater, and even more preferably 1.5 or greater. Furthermore, the same difference measured 3.5 hours before to 4.5 hours before (particularly, 4 hours before) is preferably 1.1 or greater, more preferably 1.2 or greater, and even more preferably 1.3 or greater. The same applies also to the selection criteria 4 and 5.

With regard to the selection criterion 6, it is one of preferred embodiments of the invention that the difference in area between the female pronucleus and the male pronucleus measured immediately before the time of occurrence of male and female pronuclear membrane breakdown as the reference is less than 40 µm²; however, the criterion is not limited to this. For example, the same difference is less than 45 µm², more preferably less than 40 µm², and even more preferably 35 µm².

With regard to the selection criterion 7, the condition "immediately after to 8 hours after" may also be, for example, "immediately after to 4 hours after", "immediately after to 6 hours after", "immediately after to 10 hours after", or "immediately after to 12 hours after".

The software of the invention can be used to provide a means for executing a process including a step of analyzing an image of a fertilized egg, determining the areas of the female pronucleus and the male pronucleus, and calculating the difference of the areas; and a step of storing the obtained measured values of the area difference to be readable at any time as needed. The software can be recorded in a recording medium and supplied to consumers. The recording medium used at this time is not particularly limited; however, recording media based on electronic means such as a hard disk drive and a CD-ROM can be suitably used.

An apparatus for screening a fertilized egg, the apparatus having incorporated therein a recording medium in which the software of the invention is recorded, will be described in detail below. This apparatus includes a microscope; a digital camera for capturing images of a fertilized egg observed under the microscope; a memory for storing the images of the fertilized egg captured with the digital camera; a recording medium having a software recorded therein, the software being intended for analyzing the images stored in the memory; and a display unit for displaying the results obtained by the analysis.

The microscope included in the apparatus is to observe the female pronucleus and the male pronucleus. The microscope used in this case is not particularly limited so long as the female pronucleus and the male pronucleus in a fertilized egg can be observed under the microscope; however, for example, the microscope is an optical microscope or a phase contrast microscope. The magnification ratio of the microscope is preferably 15 to 25 times.

The images of a fertilized egg observed under the microscope are observed with a digital camera. The digital camera is disposed adjacently to members including the ocular lens of the microscope so that the digital camera can capture the images of a fertilized egg observed under the microscope. The images captured with the digital camera are stored in the memory. The memory may be disposed as an independent member or may be disposed in the recording medium as a memory block. The images stored in the memory are recorded in the recording medium and analyzed by the software, and thereby the area of the female pronucleus, the area of the male pronucleus, and the difference of these areas are calculated.

The area of the female pronucleus, the area of the male pronucleus, and the difference of these areas thus calculated can be displayed in the display unit. The display unit includes a screen for displaying the analysis results, and preferably, the display unit includes a liquid crystal display screen. A fertilized egg appropriate for transplantation can be selected based on the numerical values displayed on the display unit. At this time, the selection criteria may be stored in the memory of the software, and whether a fertilized egg satisfies the selection criteria may be displayed on the display unit.

The observation of a fertilized egg under a microscope is conducted over time, and the measurement interval is, for example, every 5 minutes, every 10 minutes, every 15 minutes, or every 20 minutes. Therefore, it is difficult to take out the fertilized egg from the cell incubator and observe the fertilized egg under the microscope at every measurement time. This problem is solved by incorporating the cell incubator into the apparatus. The cell incubator is disposed in the apparatus such that the fertilized egg cultured on a culture plate is always within the field of view of the microscope when the microscope is focused.

Figure 3:
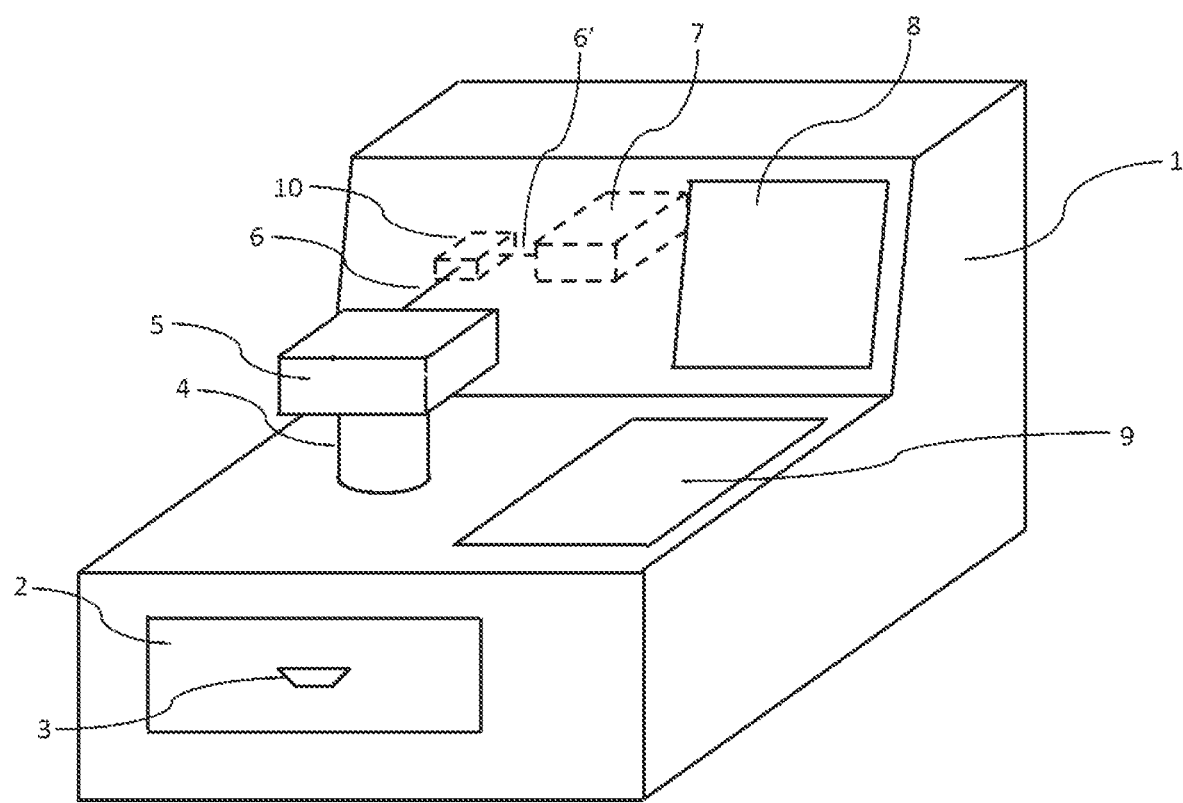
FIG. 3 is a schematic external perspective view of an apparatus according to an embodiment of the invention.

An embodiment of the apparatus that includes a microscope; a digital camera for capturing images of a fertilized egg observed under the microscope; a memory for storing the images of a fertilized egg captured with the digital camera; a recording medium having a software recorded therein, the software being intended for analyzing the images stored in the memory; a display unit for displaying the results obtained by the analysis; and a cell incubator, is schematically illustrated in FIG. 3. The present apparatus includes, inside the main body of the apparatus, a cell incubator (not shown in the diagram) in which fertilized eggs can be cultured. Taking cells in and out from the cell incubator is conducted through a cell incubator opening/closing door (2) located at the front face of the main body (1). A user of the present apparatus can access the inside of the cell incubator by holding a handgrip (3) and then pulling out the cell incubator opening/closing door (2) to the front face. A culture plate including a fertilized egg is mounted inside the cell incubator. In the upper part of the cell incubator, a microscope (4) is disposed so as to be capable of observing the fertilized egg in culture at any time as needed. Although not shown in the diagram, the object lens of the microscope (4) is inside the main body (1), and the microscope is focused on the fertilized egg on the culture plate. A digital camera (5) is disposed so as to be capable of capturing the images obtained under the microscope (4). The images captured by the digital camera (5) are transmitted to a memory (10) inside the main body (1) through a cable (6) and are stored in the memory (10). The images stored in the memory (10) are transmitted to a recording medium (7) through a cable (6').

In the recording medium (7), a software that can respectively recognize the male pronucleus and the female pronucleus in the images of the fertilized egg thus captured, measure the diameter in the horizontal direction and the diameter in the vertical direction of these pronuclei, and calculate the respective areas of the male pronucleus and the female pronucleus, and the difference of these areas, is recorded.

An image of a fertilized egg recorded in the recording medium (7), the respective areas of the male pronucleus and the female pronucleus, and the difference of these areas can be displayed on a display section (8) of a liquid crystal display screen. By having the selection criteria for fertilized eggs recorded in advance in the recording medium, a cell appropriate for transplantation can be selected by the software based on the respective areas of the male pronucleus and the female pronucleus, and the difference of these areas, and the results can be displayed on the display section (8). Control of the apparatus is performed using a control panel (9).

EXAMPLES

Hereinafter, the invention will be described in more detail by way of Examples; however, the invention is not intended to be limited to the Examples.

[Example 1] Clinical Protocol

Seventy-one patients were registered. These patients were subjected to transplantation of freeze-thawed blastocysts under hormone replacement therapy (HRT) with estrogen and progesterone.

As a pretreatment cycle, the patients received a treatment based on a long protocol. That is, use of 600 µg of gonadotropin-releasing hormone (GnRH) agonist was initiated on day 7 of the hyperthermic phase in the cycle before treatment, and from day 3 of menstruation and thereafter, the patients were subjected to daily stimulation of ovaries with follicle-stimulating hormone (FSH preparation or HMG preparation) until the diameter of the largest subordinate follicle reached 18 mm. When the diameter of the largest subordinate follicle exceeded 18 mm, ovulation was triggered. 5,000 units of human chorionic gonadotropin (hCG) was intramuscularly injected, and ova were collected transvaginally under ultrasonographic guidance 36 hours after the injection. The follicles were measured by ultrasonic scanning (Mitsubishi RDF173H).

The collected ova were fertilized by an insemination method or an intracytoplasmic sperm injection method. Fertilized eggs were cultured in a 50-µL small droplet of BlastAssist System medium 1 [containing synthetic serum replacement (SSR), human plasma albumin, glucose, sodium pyruvate, lactate, potassium sulfate, magnesium sulfate, sodium chloride, sodium hydrogen phosphate, non-essential amino acids, L-glutamine, taurine, sodium bicarbonate, HEPES, 50 mg/L streptomycin, 50,000 IU/L penicillin, and Phenol Red; MediCult A/S, Jyllinge, Denmark], and early embryos were obtained on day 2. Next, one to four of the early embryos thus obtained were cultured in a 50-µL small droplet of BlastAssist System medium 2 [containing synthetic serum replacement (SSR), human plasma albumin, glucose, sodium pyruvate, lactate, potassium sulfate, magnesium sulfate, sodium chloride, sodium hydrogen phosphate, essential amino acids, non-essential amino acids, L-glutamine, taurine, sodium bicarbonate, 50 mg/L streptomycin, 50,000 IU/L penicillin, and Phenol Red; MediCult A/S, Jyllinge, Denmark], that is, in an amount of medium of 12.5 to 50 µL per embryo, under a coating layer of mineral oil (Oil Embryo Culture, Irvine Scientific Santa Ana Calif. USA) for another three days, that is, up to day 5 in total. Thus, blastocysts were obtained. As the culture plate, FALCON353002 Tissue Culture Dish (Becton Dickinson, Franklin Lakes USA) was used. The culture of the embryos was carried out in an incubator (TE-HER PRODUCT $O_2.CO_2$ incubator CP 02-1800 series, Hirasawa Works Co., Ltd.) set at 5% $CO_2$, 5% $O_2$, 90% $N_2$, 37° C., and 100° humidity. The blastocysts obtained in this course of culture were transplanted into the uterine cavity. The subsequent birth status of the transplanted patients was followed.

[Example 2] Observation of Fertilized Eggs

The fertilized eggs after fertilization as described above were photographed every 10 minutes using an EmbryoScope™ time lapse system (Vitrolife AB), and thus images were obtained. EmbryoScope is an apparatus including a cell incubator; a microscope that can observe over time the fertilized eggs cultured in the cell incubator; a digital camera for capturing images of the fertilized eggs observed under the microscope; a recording medium for storing the images captured by the digital camera; and a liquid crystal display for displaying the images. The operation of this apparatus will be outlined below. From the images obtained using EmbryoScope, images obtained 8 hours before, 4 hours before, and immediately before the time of occurrence of male and female pronuclear membrane breakdown as the reference were selected, and the areas of the female pronucleus and the male pronucleus projected in these images were determined. The areas of the female pronucleus and the male pronucleus (collectively referred to as pronucleus) were determined by the following calculation formula: Area of pronucleus=$\pi \times \frac{1}{2} \times$diameter in horizontal direction$\times \frac{1}{2} \times$ diameter in vertical direction (µm$^2$). Furthermore, the areas of the female pronucleus and the male pronucleus immediately after and 8 hours after the time of occurrence of pronuclear formation as the reference were respectively determined.

[Example 3] Analysis of Area of Pronucleus

The values of the areas of pronuclei obtained in Example 2 were grouped on the basis of the fertilized eggs fertilized by the insemination method (IVF) and the intracytoplasmic sperm injection method (ICSI), and the average values were determined. Furthermore, each of the groups was further divided into a group that gave birth after transplantation and a group that did not give birth (four groups in total). For each of the groups, changes in the areas and the female pronucleus and the male pronucleus immediately before, 4 hours before, and 8 hours before the time of occurrence of male and female pronuclear membrane breakdown as the reference are shown in FIG. 1A, FIG. 1B, FIG. 2A, and FIG. 2B.

The results shown in FIG. 1A, FIG. 1B, FIG. 2A, and FIG. 2B reveal that for both IVF and ICSI, in the group that gave birth, the differences in area between the female pronucleus and the male pronucleus measured 8 hours before, 4 hours before, and immediately before the time of occurrence of male and female pronuclear membrane breakdown as the reference were reduced over time, whereas in the group that did not give birth, there was almost no change recognized in the differences in area between the female pronucleus and the male pronucleus measured 8 hours before, 4 hours before, and immediately before the time of occurrence of male and female pronuclear membrane breakdown as the reference.

With regard to the IVF group, in the group that gave birth, when the difference in area between the female pronucleus and the male pronucleus measured immediately before the time of occurrence of male and female pronuclear membrane breakdown as the reference was designated as 1, the same differences measured 8 hours before and 4 hours before the time of occurrence as the reference were 2.08 and 1.80, respectively.

Furthermore, with regard to the ICSI group, in the group that gave birth, when the difference in area between the female pronucleus and the male pronucleus measured immediately before the time of occurrence of male and female pronuclear membrane breakdown as the reference was designated as 1, the same differences measured 8 hours before and 4 hours before the time of occurrence as the reference were 1.78 and 1.44, respectively.

With regard to the IVF group, in the group that gave birth, the difference in area between the female pronucleus and the male pronucleus measured immediately before the time of occurrence of male and female pronuclear membrane breakdown as the reference was 30 µM', and with regard to the ICSI group, in the group that gave birth, the same difference was 20.6 µm$^2$.

Furthermore, in the group that gave birth in the IVF group as well as in the group that gave birth in the ICSI group, the area ratio of the female pronucleus and the male pronucleus (male pronucleus/female pronucleus) in the period from immediately after to 6 hours after the pronuclear formation was always greater than 1 in both cases.

[Example 4] Setting of Selection Criteria for Fertilized Eggs

From the results of Example 3, selection criteria for fertilized eggs to be used for transplantation can be prepared for IVF. An example thereof is shown in Table 4. Selection criteria 1 to 5 can be used singly or in combination, and for example, any of the selection criteria 1 to 4 may be combined with the selection criterion 5. Furthermore, any of the selection criteria 1 to 4 may be combined with the selection criterion 5, and the resulting combination may be further combined with selection criterion 6.

TABLE 4

Selection criteria for fertilized eggs that have been fertilized by IVF

| | |
|---|---|
| Selection criterion 1 | The differences in area between the female pronucleus and the male pronucleus measured immediately before, 8 hours before, and 4 hours before the time of occurrence of male and female pronuclear membrane breakdown as a reference are reduced over time. |
| Selection criterion 2 | When the difference in area between the female pronucleus and the male pronucleus measured immediately before the time of occurrence of male and female pronuclear membrane breakdown as the reference is designated as 1, the same differences measured 8 hours before and 4 hours before the time of occurrence as the reference are 1.6 or greater and 1.4 or greater, respectively. |
| Selection criterion 3 | When the difference in area between the female pronucleus and the male pronucleus measured immediately before the time of occurrence of male and female pronuclear membrane breakdown as the reference is designated as 1, the same difference measured 8 hours before the time of occurrence as the reference is 1.6 or greater. |
| Selection criterion 4 | When the difference in area between the female pronucleus and the male pronucleus measured immediately before the time of occurrence of male and female pronuclear membrane breakdown as the reference is designated as 1, the same difference measured 4 hours before the time of occurrence as the reference is 1.4 or greater. |
| Selection criterion 5 | The difference in area between the female pronucleus and the male pronucleus measured immediately before the time of occurrence of male and female pronuclear membrane breakdown as the reference is less than 40 $\mu m^2$. |
| Selection criterion 6 | The area ratio of the female pronucleus and the male pronucleus (male pronucleus/female pronucleus) measured at any time point in the period from immediately after to 8 hours after the time of occurrence of pronuclear formation as a reference is always greater than 1. |

From the results of Example 3, selection criteria for fertilized eggs to be used for transplantation can be prepared for ICSI. An example thereof is shown in Table 5. Selection criteria 1 to 5 can be used singly or in combination, and for example, any of the selection criteria 1 to 4 may be combined with the selection criterion 5. Furthermore, any of the selection criteria 1 to 4 may be combined with the selection criterion 5, and the resulting combination may be further combined with selection criterion 6.

TABLE 5

Selection criteria for fertilized eggs that have been fertilized by ICSI group

| | |
|---|---|
| Selection criterion 1 | The differences in area between the female pronucleus and the male pronucleus measured immediately before, 8 hours before, and 4 hours before the time of occurrence of male and female pronuclear membrane breakdown as a reference are reduced over time. |
| Selection criterion 2 | When the difference in area between the female pronucleus and the male pronucleus measured immediately before the time of occurrence of male and female pronuclear membrane breakdown as the reference is designated as 1, the same differences measured 8 hours before and 4 hours before the time of occurrence as the reference are 1.4 or greater and 1.2 or greater, respectively. |
| Selection criterion 3 | When the difference in area between the female pronucleus and the male pronucleus measured immediately before the time of occurrence of male and female pronuclear membrane breakdown as the reference is designated as 1, the same difference measured 8 hours before the time of occurrence as the reference is 1.4 or greater. |
| Selection criterion 4 | When the difference in area between the female pronucleus and the male pronucleus measured immediately before the time of occurrence of male and female pronuclear membrane breakdown as the reference is designated as 1, the same difference measured 4 hours before the time of occurrence as the reference is 1.2 or greater. |
| Selection criterion 5 | The difference in area between the female pronucleus and the male pronucleus measured immediately before the time of occurrence of male and female pronuclear membrane breakdown as the reference is less than 30 $\mu m^2$. |
| Selection criterion 6 | The area ratio of the female pronucleus and the male pronucleus (male pronucleus/female pronucleus) measured at any time point in the period from immediately after to 8 hours after the time of occurrence of pronuclear formation as a reference is always greater than 1. |

INDUSTRIAL APPLICABILITY

According to the invention, a software and an apparatus that can be used as means for increasing the success rate of in vitro fertilization can be provided.

EXPLANATION OF SIGNS

1 main body
2 cell incubator opening/closing door
3 handgrip
4 microscope
5 digital camera
6 cable
6' cable
7 recording medium
8 display section
9 control panel
10 memory

The invention claimed is:
1. A method, comprising:
capturing an image of a fertilized egg being cultured such that images of the fertilized egg are captured with a predetermined interval; and
causing a computer to perform a method for analyzing an image of the fertilized egg, comprising:
detecting a male pronucleus and a female pronucleus in the images of the fertilized egg captured;

measuring areas of the female pronucleus and the male pronucleus comprising measuring a diameter in a horizontal direction and a diameter in a vertical direction of the female pronucleus and the male pronucleus, and calculating respective areas of the male pronucleus and the female pronucleus according to the following formula:

area of pronucleus=$\pi \times \frac{1}{2} \times$diameter in horizontal direction$\times \frac{1}{2} \times$diameter in vertical direction ($\mu m^2$), by designating the maximum width in the horizontal direction of the pronucleus as the diameter in the horizontal direction, and designating the maximum width in the vertical direction as the diameter in the vertical direction, wherein the areas of the female pronucleus and the male pronucleus are measured over time with intervals of every 5 minutes to every 1 hour, measuring a first area difference between the female pronucleus and the male pronucleus from an image of a fertilized egg captured at a point of time in a period from 1 hour before to 10 hours before a time of occurrence of male and female pronuclear membrane breakdown;

measuring a second area difference between the female pronucleus and the male pronucleus from an image of a fertilized egg captured at a point of time in a period from immediately before to 20 minutes before the time of occurrence of the male and female pronuclear membrane breakdown;

selecting a fertilized egg to be transplanted into the uterine cavity based on measured values of the first area difference and the second area difference, wherein the selecting comprises selecting a fertilized egg that satisfies that the second area difference is less than 40 $\mu m^2$, and transplanting the fertilized egg into the uterine cavity.

2. The analytical method according to claim 1, wherein the selecting comprises selecting the fertilized egg that further satisfies that the second area difference is smaller than a difference in area between the female pronucleus and the male pronucleus measured at a point of time in a period from 7 hours before to 10 hours before the time of occurrence of the male and female pronuclear membrane breakdown.

3. The analytical method according to claim 1, wherein the selecting further comprises selecting the fertilized egg that further satisfies that a difference in area measured at a point of time in a period from 7.5 hours before to 8.5 hours before the time of occurrence of the male and female pronuclear membrane breakdown is 1.3 times or greater than the second area difference.

4. The analytical method according to claim 1, wherein the selecting further comprises selecting the fertilized egg that further satisfies that an area ratio of the female pronucleus and the male pronucleus measured at any point of time in a period from immediately after to 8 hours after a time of occurrence of pronuclear formation is greater than 1.

5. The analytical method according to claim 2, wherein the selecting further comprises selecting the fertilized egg that further satisfies that an area ratio of the female pronucleus and the male pronucleus measured at any point of time in a period from immediately after to 8 hours after a time of occurrence of pronuclear formation is greater than 1.

6. The analytical method according to claim 1, wherein the capturing of the image is conducted at an interval of 1 minute to 5 minutes between each capturing.

7. The analytical method according to claim 2, wherein the capturing of the image is conducted at an interval of 1 minute to 5 minutes between each capturing.

8. The analytical method according to claim 3, wherein the capturing of the image is conducted at an interval of 1 minute to 5 minutes between each capturing.

9. The analytical method according to claim 4, wherein the capturing of the image is conducted at an interval of 1 minute to 5 minutes between each capturing.

10. The analytical method according to claim 5, wherein the capturing of the image is conducted at an interval of 1 minute to 5 minutes between each capturing.

11. A method, comprising:

subjecting a patient to transplantation of freeze-thawed blastocysts under hormone replacement therapy (HRT) with estrogen and progesterone, comprising in a pretreatment cycle, initiating application of gonadotropin-releasing hormone (GnRH) agonist on day 7 of the hyperthermic phase in the cycle before treatment, and from day 3 of menstruation and thereafter, subjecting the patient to daily stimulation of ovaries with follicle-stimulating hormone, until a diameter of the largest subordinate follicle reached a predetermined value, and triggering ovulation, intramuscularly injecting human chorionic gonadotropin (hCG), and transvaginally collecting ova under ultrasonographic guidance after the injection, and measuring follicles by ultrasonic scanning, fertilizing the collected ova by an insemination method or an intracytoplasmic sperm injection method and culturing fertilized eggs in a medium 1 to obtain early embryos, capturing an image of a fertilized egg being cultured such that images of the fertilized egg are captured with a predetermined interval;

detecting a male pronucleus and a female pronucleus in the images of the fertilized egg captured;

measuring a diameter in a horizontal direction and a diameter in a vertical direction of the male pronucleus and the female pronucleus;

calculating respective areas of the male pronucleus and the female pronucleus according to the following formula:

area of pronucleus=$\pi \times \frac{1}{2} \times$diameter in horizontal direction$\times \frac{1}{2} \times$diameter in vertical direction ($\mu m^2$), by designating the maximum width in the horizontal direction of the pronucleus as the diameter in the horizontal direction, and designating the maximum width in the vertical direction as the diameter in the vertical direction, wherein the areas of the female pronucleus and the male pronucleus are measured over time with intervals of every 5 minutes to every 1 hour, calculating a first area difference between the respective areas of the female pronucleus and the male pronucleus from an image of the fertilized egg captured at a point of time in a period from 1 hour before to 10 hours before a time of occurrence of male and female pronuclear membrane breakdown;

calculating a second area difference between the respective areas of the female pronucleus and the male pronucleus from an image of the fertilized egg captured at a point of time in a period from immediately before to 20 minutes before the time of occurrence of the male and female pronuclear membrane breakdown; and selecting a fertilized egg for transplantation based on calculated values of the first area difference and the second area difference, wherein the selecting comprises selecting the fertilized egg that satisfies that the second area difference is less than 40 μm$^2$, culturing at least one of the obtained early embryos obtained from the selected fertilized egg in a medium 2 on a culture plate in an incubator, and obtaining blastocysts, and transplanting the blastocysts obtained in the culturing of the selected fertilized egg into the uterine cavity, and determining a subsequent birth status of the transplanted patients.

* * * * *